United States Patent [19]
Ogino et al.

[11] 4,411,624
[45] Oct. 25, 1983

[54] DENTAL IMPLANT

[75] Inventors: Makoto Ogino, Yokohama; Takamitsu Fujiu, Tokyo; Michio Kariya, Yokohama; Takeo Ichimura, Tokyo, all of Japan

[73] Assignee: Nippon Kogaku K.K., Tokyo, Japan

[21] Appl. No.: 309,513

[22] Filed: Oct. 7, 1981

[30] Foreign Application Priority Data

Oct. 29, 1980 [JP] Japan .................. 55-151964

[51] Int. Cl.$^3$ .............................................. A61C 8/00
[52] U.S. Cl. ................................ 433/173; 433/201
[58] Field of Search ................... 433/201, 175, 173

[56] References Cited
U.S. PATENT DOCUMENTS

| | | | |
|---|---|---|---|
| 3,922,155 | 11/1975 | Bromer et al. | 433/201 |
| 4,195,409 | 4/1980 | Chic | 433/201 |
| 4,199,864 | 4/1980 | Ashman | 433/175 |
| 4,259,072 | 3/1981 | Hirabayashi | 433/201 |

FOREIGN PATENT DOCUMENTS

| | | | |
|---|---|---|---|
| 2824214 | 12/1979 | Fed. Rep. of Germany | 433/201 |
| 2928007 | 1/1981 | Fed. Rep. of Germany | 433/201 |

Primary Examiner—Robert Peshock
Attorney, Agent, or Firm—Fitzpatrick, Cella, Harper & Scinto

[57] ABSTRACT

A dental implant is disclosed which comprises a dental root part to be embedded in a jaw bone alone or in combination with a dental crown part or a dental crown support part. At least a major portion of the surface of the dental root part to be in contact with the jaw bone is formed of a biologically active material. The contour of the surface of the dental root part is rotationally symmetrical with its diameter being constant or decreased monotonously from its one end, that is, the collum dentis portion to the other end, that is, the root end portion. The root end portion is smoothly closed.

1 Claim, 12 Drawing Figures

DENTAL IMPLANT

BACKGROUND OF THE INVENTION

1. Field of the Invention

The present invention relates to a dental implant, and more particularly to an implant of the type which comprises a dental root to be embedded in a jaw bone alone or in combination with a dental crown or a dental crown support.

2. Description of Prior Arts

Hitherto there have been proposed various dental implants for replacing a lost tooth or lost teeth, and some of them have already been accepted for practical use. In many of these known dental implants, the basic material used for making the dental implant is metal or ceramics which is inactive in a living body. They are so designed as to be mechanically supported by the jaw bone. In other words, almost all of the known dental implants rely on a mechanical bonding force between the implant and the jaw bone. For this reason, the known dental implants are complicated in shape and are difficult to manufacture. In addition, they are apt to slip out due to the resorption of the jaw bone caused by the partial concentration of stress on a part thereof.

Recently it has been reported in the art that a very useful dental implant can be obtained by forming its dental root part with a biologically active material such as biologically active glass or glass-ceramics (cf. U.S. Pat. Nos. 4,159,358 and 4,234,972). Such biologically active material is able chemically to combine with bone. Therefore, if a dental implant is made of such biologically active material, then it is possible rigidly to fix the implant to the jaw bone without the need for mechanical bonding, and it enables simplification of the shape of the implant to a great extent.

However, the bonding strength between biologically active material and bone has a certain limit. Although the dental implant using a biologically active material can be designed to have a very simple form, there remains the possibility that the chemical bond between the implant and the bone may be broken and the implant may come out when a large stress is applied thereto by biting, for example, and the stress is concentrated on a limited portion of the dental implant.

SUMMARY OF THE INVENTION

Accordingly, we have conceived and contribute by the present invention an improved dental implant making use of the chemical bond between a biologically active material and a bone.

One aspect of our invention resides in the fact that such dental implant has a dental root so designed as to bond with the jaw bone with a possible maximum stability in view of dynamics.

The dental implant according to the invention is, therefore, characterized in its improved form of the dental root to be embedded in the jaw bone. The dental implant is composed of the dental root alone or a combination of the dental root and a dental crown or a dental crown support part. The dental root is made of a biologically active material at least at a major portion if its surface to be positioned in contact with the jaw bone. The external appearance of the dental root is rotationally symmetrical and the diameter thereof is constant or decreased monotonously from the collum dentis, that is, one end of the dental root to the root end portion, that is, the other end of the dental root. At the root end portion, the dental root is smoothly closed.

There has thus been outlined rather broadly the more important features of the invention in order that the detailed description thereof that follows may be better understood, and in order that the present contribution to the art may be better appreciated. There are, of course, additional features of the invention that will be described hereinafter and which will form the subject of the claims appended hereto. Those skilled in the art will appreciate that the conception upon which this disclosure is based may readily be utilized as a basis for the designing of other structures for carrying out the several purposes of the invention. It is important, therefore, that the claims be regarded as including such equivalent constructions as do not depart from the spirit and scope of the invention.

BRIEF DESCRIPTION OF THE DRAWINGS

Specific embodiments of the invention have been chosen for purposes of illustration and description, and are shown in the accompanying drawings, forming a part of the specification wherein.

DETAILED DESCRIPTION OF THE INVENTION

For a dental implant using a biologically active material, the most important factor is the dynamic stability of the implant after it has been implanted in a jaw bone and a sufficient bond has been formed therebetween. Generally speaking, the dynamic stability of a dental implant is determined by the resistance to the level of stress between the bonding surface of the bone and the biologically active material. Therefore, it is essential that the magnitude and distribution of the stress which may be applied onto the interface between the biologically active material and bone be thoroughly considered and that the shape of the dental implant be designed in such manner that no great stress may be applied to the area in the vicinity of the interface.

To know the magnitude and distribution of forces applied to a dental implant there may be used various computing methods. However, the method most reliable at present for this purpose is the so-called infinite element computing method. We have conducted a number of computations to find out the magnitude and distribution of stress. To this end, we have made some models of dental implant and considered various shapes of dental implant employing the infinite element method. An example of the model used for this computation is shown in FIG. 1.

Figure 1:
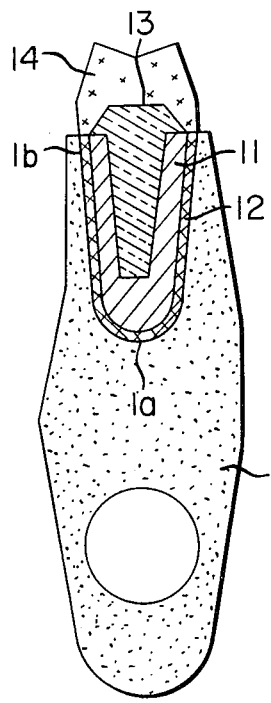
FIG. 1 is a schematic sectional view of a denture as a computation model.

In FIG. 1, the denture comprises a root core 11 covered with a layer of biologically active glass 12, a metal post core 13 inserted into a recessed portion of the root core 11 and a dental crown 14 mounted on the metal post core 13. The biologically active glass layer 12 covers the surface area of the core 11 extending from its lower root end portion 1a to its collum dentis 1b. The dental root is implanted in a jaw bone 2. The metal post core 13 is fitted into the root core 11 in the manner shown in FIG. 1. The dental crown 14 mounted on the metal core 13 is made of resin.

Several different models as shown in FIG. 1 have been prepared for calculations employing the infinite element method. The results of the calculations have led us to the conclusion that the shearing stress applied to the area near the interface between the jaw bone and the biologically active material can be minimized and therefore a high dynamic stability can be obtained when the dental root is designed to satisfy the following conditions as the dental root 1 shown in FIG. 2 does:

The dental root should have a form of a rotationally symmetrical body basically composed of a truncated cone and a semi-sphere jointed together;

The dental root should have a diameter decreasing monotonously from one end thereof, namely the collum dentis 1b to the other end, namely the root end 1a; and The root end portion 1a should be closed smoothly, for example, forming a semi-sphere.

Figure 2:
FIG. 2 is a schematic perspective view of a dental root.
Figure 3:
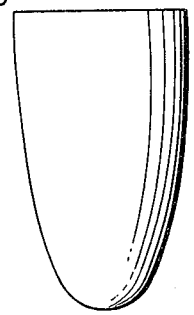
FIGS. 3 and 4 are side elevations of dental roots having different shapes.
Figure 4:
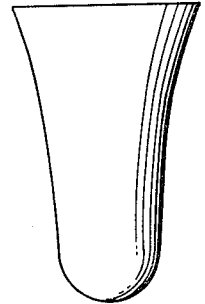

The form of the side surface of the preferred dental root, excepting the root end portion, is never limited only to a cone as shown in FIG. 2. It may be, for example, cylindrical. Also, it may be in a form as shown in FIG. 3 where the changing rate of diameter increases gradually toward the root end 1a. Further, it may be a form as shown in FIG. 4 wherein the changing rate of diameter is larger at the area near the collum dentis 1b and decreases toward the root end 1a. By using such form of the dental root, the concentration of stress may be minimized and therefore the stability of the dental root can be improved. In any case, the root end 1a should be closed smoothly. As a whole, the forms of dental root shown in FIGS. 3 and 4 may be considered to be slight modifications of the basic form shown in FIG. 2. Therefore, it should be understood that the form shown in FIG. 2 represents the basic form of the dental root according to the invention.

While we have conducted the computation using, as the computation models, those dental roots as shown in FIG. 2 which comprise a metal root core and a layer of biologically active material applied on the core, it is to be understood that the internal structure of the dental root is of no critical importance. In general, the bonding strength between a root core made of metal or other material and a biologically active material is larger than that between the biologically active material and a bone. Therefore, the thing to be considered is only the bonding strength between the bone and the biologically active material. The internal structure of the dental root has no substantial effect on the dynamic stability of the implant after implantation. Even when the whole body of a dental root is composed of only biologically active material, the stability of the dental implant can be improved by designing it to have a form as described above.

In the above computation concerning the preferred form of a dental root, we have made a study also on the distribution of stress applied to the dental implant. For this purpose, the radius of the collum dentis 1b ($r_0$) and the radius of curvature of the root end 1a ($r_1$) were variously changed to alter the shape of the dental root for which the model computation was carried out. This study has taught us that the degree of the stress concentration on the root end portion increases remarkably when it is shaped into a sharp form similar to that of the root of a natural tooth. More concretely, we have made two models of dental roots for the study and applied onto them a pressure equivalent to a load of 60 kg on the first molar. The two models had the same radius at the collum dentis portion 1b. Namely, $r_0=1$. But, the two models had different curvature radii at the root end portion 1a. Namely, $r_1=0.26$ for one model and $r_1=0.7$ for the other to the same radius of the collum dentis portion, $r=1$. For both of the models, the maximum value Tm of shearing stesss at the interface between the jaw bone and the biologically active material was calculated. The following table shows the result of the calculation:

| $r_0$ | $r_1$ | Tm | | $(r_1/r_0)^2$ |
|---|---|---|---|---|
| 1 | 0.26 | 1.85 | kg/mm² | 0.07 |
| k | 0.7 | 0.6 | kg/mm² | 0.49 |

Figure 5:
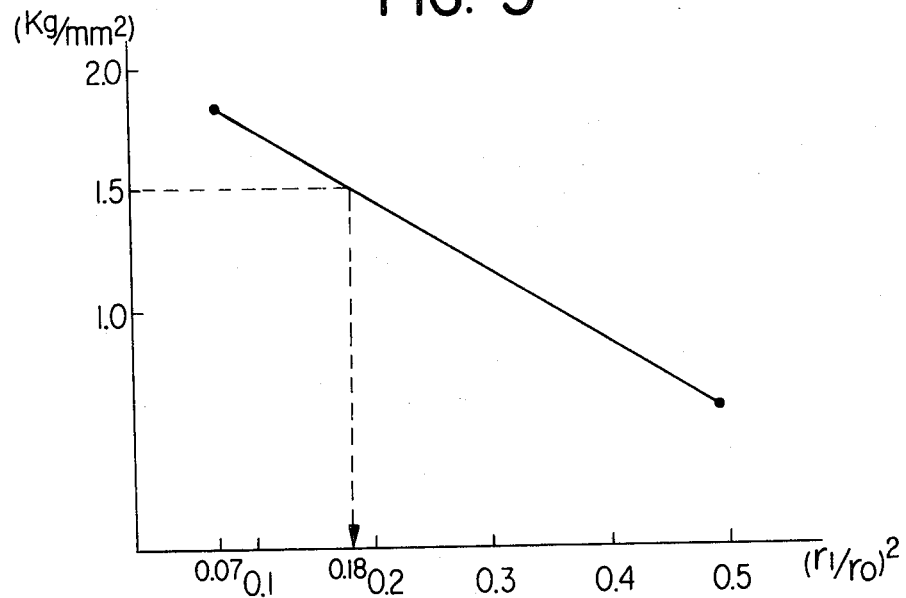
FIG. 5 is a graph showing the relation between the form of dental root and the maximum value of shearing stress.

FIG. 5 is a graphic illustration of the result wherein $(r_1/r_0)^2$ is plotted on the abscissa and the maximum shearing stress, Tm on the ordinate. As a linear approximate, the maximum shearing stress may be considered to be proportional to the surface area of the root end portion, that is, to $(r_1/r_0)^2$. Therefore, the correlation between the form of dental root and the maximum shearing force can be found by binding two points on the graph with a straight line. From the graph shown in FIG. 5 is it clearly seen that the maximum shearing stress, Tm decreases with increasing the radius of the root end portion, $r_1$ relative to $r_0$.

Since the shear strength of the chemical bond at the interface between biologically active glass and bone (Td) is experimentally known Td=1.5 kg/mm², it is possible to know the value of $(r_1/r_0)^2$ corresponding to the value of Td by reading the graph, which value is 0.18. Consequently, it is expected that the chemical bond at the interface may be broken when $r_1/r_0$ is larger than 0.42. Therefore, to obtain a highly stable dental root, it is desirable that the dental root using biologically active glass or biologically active glass-ceramics having the same property should be designed to satisfy the condition, $r_1/r_0>0.42$.

According to the feature of the invention, the stress concentration can be reduced even when $r_1=r_0$, that is, even when the dental root is cylindrical at the portion extending from its collum dentis to the beginning of the root end portion. However, the use of such dental root having a cylindrical form involves some drawback. In this case, since the bore drilled in the jaw bone at the operation for implantation is also to be cylindrical, the dental root fitted in the bore is apt to move in the axial direction of the cylinder. Therefore, the fitting accuracy is not as precise as compared with the case of a dental root whose diameter is decreased monotonously from the collum dentis to the root end portion. For this reason, it is preferable that the value of $r_1/r_0$ be less than 1.

Hereinafter, preferred embodiments of the invention will be described with reference to FIGS. 6 to 12.

Figure 6:
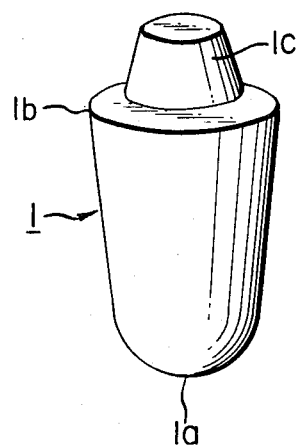
FIG. 6 is a perspective view of a first embodiment of the invention.

FIG. 6 is a perspective view of a dental implant showing a first embodiment of the invention. Generally designated by 1 is a dental root part. 1b is the collum dentis portion of the dental root and 1a is the root end portion. 1c is a support part for supporting a dental crown (not shown). The dental root part and the support part are integrally formed as a unit entirely made of a biologically active glass or glass-ceramics. Biologically active glass or glass-ceramics used in the invention is known per se. for example, there may be used those glass compositions as disclosed in U.S. Pat. Nos. 4,234,972; 3,981,736 and 4,120,730. Other preferred biologically active glass and glass-ceramics are those which have been proposed by our prior invention. The biologically active glass and glass-ceramics previously invented by us essentially comprise:

| | |
|---|---|
| $SiO_2$ | 35-60 mol % |
| $B_2O_3$ | 5-15 |
| $Na_2O$ | 10-30 |
| $CaO$ | 5-40 |
| $TiO_2$ | 0.5-10 |
| $P_2O_5$ | 0-15 |
| $K_2O$ | 0-20 |
| $Li_2O$ | 0-10 |
| $MgO$ | 0-5 |
| $Al_2O_3 + ZrO_2 + Nb_2O_5$ | 0-8 |
| $La_2O_3 + Ta_2O_5 + Y_2O_3$ | 0-8 |
| $F_2$ | 0-15 |

According to the first embodiment shown in FIG. 6, the dental root part 1 is so designed as to decrease the radius continuously from the collum dentis portion 1b to the root end portion 1a which is smoothly closed forming a semi-sphere.

Figure 7:
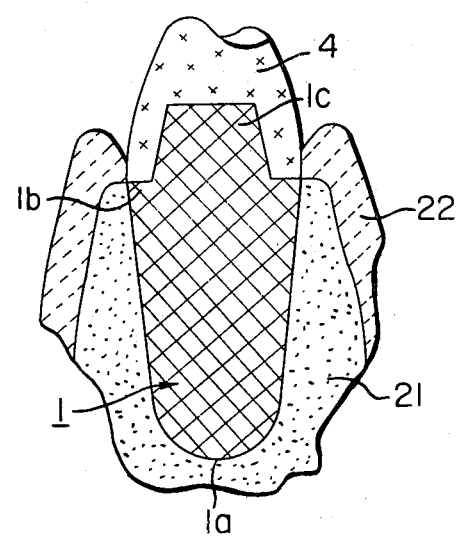
FIG. 7 is a cross-sectional view thereof with the dental implant embedded in the jaw bones.

The dental implant is implanted in a jaw bone 21 with which the dental implant is to be bonded. FIG. 7 shows the dental implant after completing a sufficient bond between the dental implant and the jaw bone. The dental root part 1 is implanted with its collum dentis portion 1b being embedded in the jaw bone 21 as shown in FIG. 7. In this position, the collum dentis portion 1b corresponds to the collum dentis of a natural tooth. After implantation, the biologically active glass or glass-ceramics of the dental root part 1 at the surface area in contact with the jaw bone begins chemically to bond with the jaw bone. Within four to eight weeks there is obtained a sufficiently large bonding strength for practical purpose. Thereafter, a dental crown 4 made of resin is mounted on the crown support part 1c and the dental crown 4 is firmly fixed to the dental root part 1 by means of a bonding agent. Finally, the epithelial tissue 22 on the jaw bone 21 developes up to the collum dentis portion 1b so as completely to isolate the dental root part 1 from the exterior and also the closing of the epithelial tissue 22 is completed.

Figure 8:
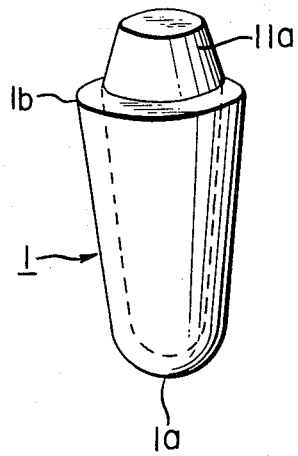
FIG. 8 shows a second embodiment.
Figure 9:
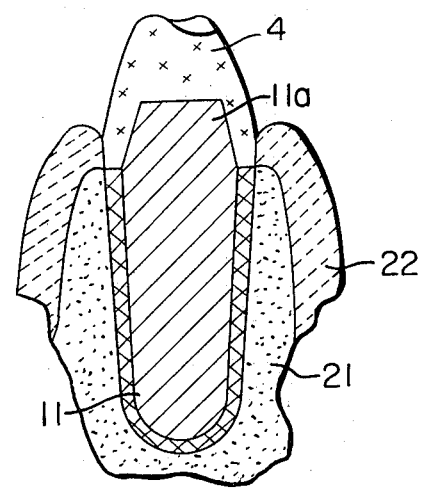
FIG. 9 is a view similar to FIG. 7 but showing the second embodiment.

FIGS. 8 and 9 show a second embodiment of the invention.

In this second embodiment, the dental root part 1 is composed of a root core 11 and a layer of biologically active glass or glass-ceramics 12 applied on the core 11. The biologically active layer 12 covers the area extending from the root end portion 1a to the collum dentis portion 1b. The dental root part 1 has a projection 11a formed on the top of the core 11. The projection 11a serves also as a support member for supporting a dental crown 4. Compared with the first embodiment, this structure of the second embodiment has a further improved mechanical strength on the whole of the dental implant including the dental root part. The root core 11 may be formed of any suitable material having an adequately high mechanical strength. Examples of such material include: stainless steel, cobalt-chromium alloy, titanium and its alloys, nobel metals such as platinum, nobel metal alloys such as platinum(90%)-rhodium(10%), molybdenum-nickel-cobalt-chromium alloy and alumina.

The higher the bonding strength between the core 11 and the biologically active layer 12, the better the dynamic stability of the dental implant as a whole. FIG. 9 shows the second embodiment implant after implantation has been completed. Like reference numerals of the first embodiment represent the same or corresponding parts and elements. Like the first embodiment, the second embodiment eliminates the concentration of stress on the interface between the jaw bone and the biologically active material. The epithelial tissue 22 is finally closed completely to provide practically sufficient stability for the dental implant.

Figure 10:
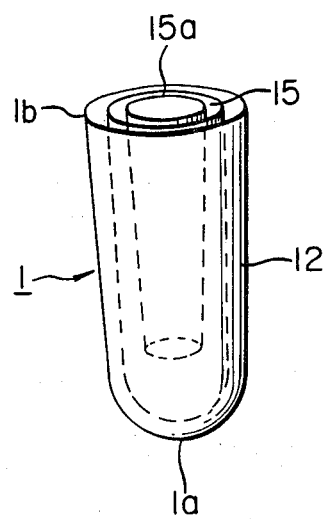
FIG. 10 shows a third embodiment.
Figure 11:
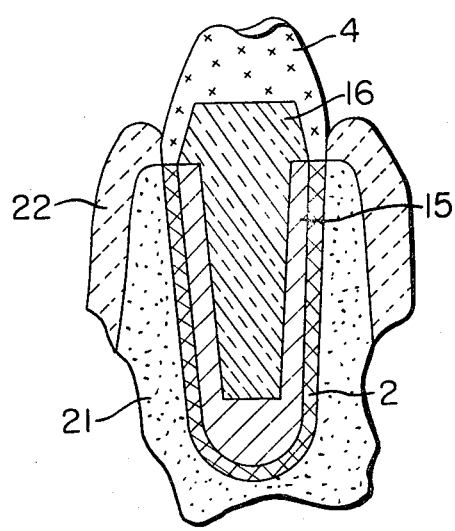
FIG. 11 is a view of the third embodiment similar to FIG. 7.

FIGS. 10 and 11 show a third embodiment of the invention wherein FIG. 10 illustrates the structure before implantation and FIG. 11 shows it after implantation.

In the third embodiment, the root core 15 has a center bore 15a for receiving a metal post-core 16. The center core 15a is in the form of a truncated cone. The root core 15 is coated with a layer of biologically active glass or glass-ceramics 12 excepting the upper end surface of the core. The biologically active layer 12 has a substantially constant thickness (about 0.2–1.0 mm). The annular upper end surface of the root core 15 is coplanar with the annular end surface of the biologically active layer 12 so that the upper end portion constitutes the collum dentis portion of the dental root.

After the biologically active layer 12 and the jaw bone 21 have been completely bonded together, the post-core 16 mentioned above is fitted into the center bore 15a of the root core 15 and cemented to the latter in the manner shown in FIG. 11. Thereafter, a dental crown 4 is mounted on and cemented to the dental root using the post-core 16 serving as a connection member. Thus, an artificial tooth is completed. In this embodiment also, the diameter of the dental root is decreased uniformly from the collum dentis portion 1b to the root end portion 1a which is closed smoothly forming a semi-sphere. Owing to this form of the dental root, the partial concentration of stress on the dental implant can be minimized and therefore the dynamic stability thereof can be improved remarkably.

Figure 12:
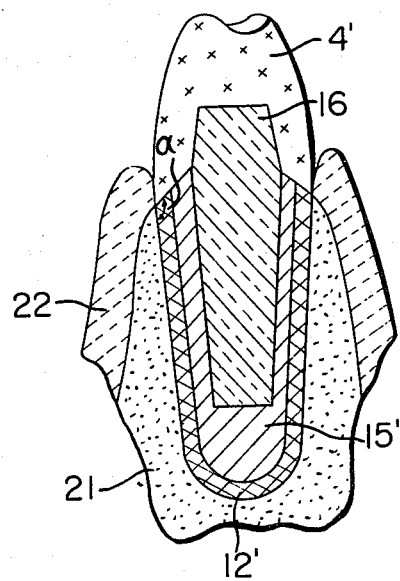
FIG. 12 is a cross-sectional view of a fourth embodiment of the invention.

FIG. 12 shows a fourth embodiment of the invention.

The structure of this fourth embodiment is essentially the same as those of the above three embodiments. This structure of the fourth embodiment also minimizes the stress concentration on the interface area between the biologically active glass or glass-ceramics thereby providing a dental implant of higher dynamic stability. The difference between the fourth embodiment and the above three embodiments is found only in the shape of the collum dentis portion of the dental root to be embedded in the jaw bone 21. As shown in FIG. 12, it often occurs that the tip end of the jaw bone in which a dental implant is to be implanted is not flat but tapered. The fourth embodiment is designed to accomodate the collum dentis portion to the shape of such jaw bone. The annular end surfaces of the root core 15' and of the biologically active layer 12' are together cut out to form an inclined roof-like end surface. When implanted, the roof-like end portion becomes contiguous with the tapered end portion of the jaw bone 21 as seen in FIG. 12. The end surface of dental crown 4' is also shaped into an internally inclined or roof-like form to match it with the end surface of the dental root. The dental crown 4' is connected with the dental root through a post-core 16 to complete an artificial tooth having a smooth contour as a whole. In this embodiment, the end surface of the dental root and the side surface of the same dental root form an obtuse angle α at the collum dentis portion of the biologically active layer. This obtuse angle α has the effect to lessen the danger of the epithelial tissue being damaged by the edge of the dental root. Therefore, in view of safety, this embodiment has an advantage over the above embodiments.

As readily understood from the foregoing, the dental implant according to the invention has many advantages over the prior art implants. According to the invention, the most dynamically stable dental implant can be obtained when biologically active material is used. The dental root part is in the form of a rotationally symmetrical body which is easy to machine with existing apparatus and tools. Therefore, the present invention makes it possible to obtain dental implants of high precision. The rotationally symmetrical form of the dental root has another advantage in that a bore necessary for implantation can be drilled in the jaw bone very easily and precisely with a dental bone drilling bar perfectly matched to the form of the dental root. Therefore, very good fitting is assured at the implanting operation. In the case of a dental implant employing a biologically active material, it is required that the dental implant should be kept motionless in the implanted position at the first stage after the implanting operation. If it moves even a little at an early stage after the operation, then no strong bonding may be obtained between the biologically active material and the jaw bone. According to the invention, since the dental implant has a very precise form and the implanting operation can be carried out with a very precise dental drilling bar proper to the dental implant, such undesirable motion at an early stage after the operation can be prevented completely. Accurate operation and good fitting are assured by using the dental implant according to the invention. This accelerates the formation of a good and strong bond between the dental implant and jaw bone.

The dental implant shown in FIGS. 10 and 11 as the third embodiment of the invention, does not have any such portion which will project over the jaw bone after the implanting operation. As there is no projecting portion, the implant can not be moved by foreign matter which otherwise strike against the dental implant. Accuracy of operation is also improved accordingly. The third embodiment is an example of the dental root a form in which the effect of the present invention becomes particularly remarkable.

While the described embodiments represent the preferred forms of the invention, obviously modifications and variations are possible in light of the above teachings. For example, all or a part of the surface of the dental root part to be in contact with a jaw bone may be roughed or made porous to increase the coefficient of friction. By doing so, the initial fixing of the implant may be further accelerated.

We believe that the construction and application of our novel dental implant will now be understood and that the several advantages thereof will be fully appreciated by those persons skilled in the art.

We claim:

1. A dental implant comprising a dental root part to be embedded in a jaw bone alone or in combination with a dental crown or a dental crown supporting part, which dental implant is characterized in that at least a substantial portion of the dental root surface to be placed in contact with the jaw bone is formed of a biologically active glass or glass-ceramic material and the contour of said dental root part is rotationally symmetrical with its diameter being monotonously decreased from one end forming the collum dentis portion of the dental root to the other end forming the root end portion which is in the form of a semi-sphere, approximately, and said dental root part is so designed as to satisfy the condition:

$$0.42 < r/r_0 < 1.0;$$

wherein, $r$ is the radius of curvature of said root end portion; and $r_0$ is the radius of said collum dentis portion of said dental root part.

* * * * *